United States Patent
Matsuo et al.

(10) Patent No.: US 7,674,143 B2
(45) Date of Patent: *Mar. 9, 2010

(54) SENSOR AND METHOD OF PRODUCING SENSOR

(75) Inventors: Kouji Matsuo, Aichi (JP); Satoshi Ishikawa, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1030 days.

This patent is subject to a terminal disclaimer.

(21) Appl. No.: 10/571,764

(22) PCT Filed: Sep. 13, 2004

(86) PCT No.: PCT/JP2004/013300

§ 371 (c)(1),
(2), (4) Date: Mar. 14, 2006

(87) PCT Pub. No.: WO2005/029058

PCT Pub. Date: Mar. 31, 2005

(65) Prior Publication Data

US 2007/0096615 A1    May 3, 2007

(30) Foreign Application Priority Data

Sep. 17, 2003    (JP)    ............... 2003-324822

(51) Int. Cl.
*H01R 4/48* (2006.01)
(52) U.S. Cl. .................................................. 439/862
(58) Field of Classification Search ............... 439/862
See application file for complete search history.

(56) References Cited

U.S. PATENT DOCUMENTS 3,417,362 A * 12/1968 Reynolds ................ 439/77
5,980,323 A * 11/1999 Bricaud et al. ............ 439/630
7,340,942 B2 * 3/2008 Matsuo et al. ............ 73/31.05
7,461,538 B2 * 12/2008 Matsuo et al. ............ 73/23.31

FOREIGN PATENT DOCUMENTS

| JP | 61-70763 U | 5/1986 |
| JP | 1-71663 U | 5/1989 |
| JP | 9-145670 A | 6/1997 |
| JP | 10-2877 A | 1/1998 |
| JP | 2002-168825 A | 6/2002 |

* cited by examiner

Primary Examiner—Tho D Ta
(74) Attorney, Agent, or Firm—Sughrue Mion, PLLC

(57) ABSTRACT

The present invention provides a sensor and a method of producing the same, which makes an electrical connection condition between an electrode terminal section of a detection element and a metallic terminal member good. The sensor includes a lead frame (metallic terminal member) that changes a support condition of supporting an element abutment section for contact with a detection element on a frame main body section, into a one-point support or a two-point support. At a first-half stage of a work for assembly of the lead frame and the detection element, the element abutment section is put in a one-point support condition relative to the frame main body section and the lead frame produces a relatively smaller resilient force, such that it becomes possible to prevent an excessively large pressure from being applied to the detection element. After the assembly work is completed, the element abutment section is put in a two-point support condition relative to the frame main body section and the lead frame produces a larger resilient force as compared with that in the one-point support condition, such that the electrical connection condition between the lead frame and the detection element can be good.

13 Claims, 7 Drawing Sheets

SENSOR AND METHOD OF PRODUCING SENSOR

TECHNICAL FIELD

This invention relates to a sensor having a detection element in the form of an axially extending plate and formed with an electrode terminal section at a rear end side and a metallic terminal member contacting the electrode terminal section thereby being electrically connected thereto to form a current path, and a method of producing such a sensor.

BACKGROUND TECHNIQUE

Heretofore, it is known a sensor having attached thereto a detection element (sensor element) in the form of an axially extending plate and formed with a detection section at a front end side to face an object to be measured. Enumerated as such a sensor are a gas sensor such as a λ (lambda) sensor, a wide-range air/fuel ratio sensor, oxygen sensor and NOx sensor, and a temperature sensor for detection of temperature.

The plate-shaped detection element is generally configured so as to have a detection section at an axial (longitudinal) front end side and electrode terminal sections at both side surfaces at a rear end side. A sensor that is regarded as one having such a detection section is configured to electrically connect a lead frame (metallic terminal member) made of an electrically conductive material to an electrode terminal section for thereby forming a portion of an electric current path for conduction of electrical current between the detection element and an external device by means of the lead frame. In the meantime, electrical currents such as detection current (detection signal) according to a result of detection by the detection element and electrical current for power supply to a heater in case the detection element has the heater flow through the electrical current path electrically connecting the detection element and the external device.

As a sensor having a lead frame is known a sensor configured to use a lead frame having a resilient contact portion that serves as a resiliently deformable leaf spring and hold a detection element within an insertion hole of a separator, with the resilient contact portion of the lead frame being in a condition of being brought into contact with the resilient contact portion of the lead frame (refer to Patent Document 1). In the meantime, the resilient contact portion is provided to the lead frame so as to be in a condition of being connected at one of opposite ends to a lead frame main body section (in a one-point support condition).

In case of a sensor with such a structure, it becomes possible to make good the connection condition between the lead frame and the electrode terminal section of the detection element by using a lead frame configured so that a resilient contact portion exerts a large resilient force. In the meantime, as a lead frame with a resilient contact portion exerting a large resilient force are enumerated, for example, a lead frame formed so as to be large in the width size, a lead frame formed so as to be large in the thickness, etc.

Patent Document 1: Unexamined Japanese Patent Publication No. 2001-188060.

However, in case a lead frame having a resilient contact portion that exerts an excessively large resilient force is used as in a prior art sensor, a large pressure more than needed is applied from the lead frame to the detection element at the time of assembly of the lead frame and the detection element, so that a damage of the detection element such as chipping or breakage may possibly be caused by that pressure.

Further, since a lead frame large in the width size requires a wide space for disposition thereof, there arises a problem that such a lead frame is not suited for use in a sensor that is needed to be small-sized. Further, in the event a lead frame large in the width size is used for a detection element formed with a plurality of electrode terminal sections that are small in the width size and positioned close to each other, there is a possibility that one lead frame is brought into contact with all the plurality of electrode terminal sections and a suitable electrical current path cannot be formed.

In the meantime, by using a lead frame that is formed small in the width side for such a detection element having a plurality of electrode terminal sections, the current path can be formed. However, a lead frame having a resilient contact portion in a one-point support condition as the above-described prior art lead frame tends to lack a resilient force if formed smaller in the width size, thus being incapable of sufficiently contacting the electrode terminal section due to the lack of resiliency and possibly causing the condition of connection with the electrode terminal section to be unstable.

SUMMARY OF THE INVENTION

The present invention has been made in view of the foregoing problems and has for its object to provide a sensor and a method of producing the same, which is hard to cause breakage of a detection element at the time of assembly with a metallic terminal member and can maintain an electrical connection between an electrode terminal section of the detection element and the metallic terminal member even when the space for disposition of the metallic terminal member is limited.

According to an aspect of the present invention, there is provided a sensor comprising a detection element in the form of an axially extending plate, having a front end side to face an object to be measured and formed with an electrode terminal section at a rear end side, and a metallic terminal member formed from a metallic sheet material and contacting the electrode terminal section thereby being electrically connected thereto to form an electrical path, wherein the metallic terminal member includes an axially extending frame main body section and a folded-back section extending while being bent to change the direction of extension, from a front end of the frame main body section axially toward a rear end side of the frame main body section and contacting the electrode terminal section of the detection element thereby being electrically connected thereto to form a current path, wherein the folded-back section includes a connection side end portion connected to a front end of the frame main body section and a frame abutment portion formed at a position closer to a rear end than the connection side end portion for abutting engagement with the frame main body section.

The sensor is configured to include the metallic terminal member having the frame main body section and the folded-back section, and the metallic terminal member contacts at least a portion thereof with the electrode terminal section of the detection element thereby forming a current path for connection between the detection element and an external circuit.

In this embodiment, the folded-back section of the metallic terminal member is formed at the connecting side end portion connected to the front end of the frame main body section and at the side closer to the rear end than the connecting side end portion and has a frame abutment portion to be abuttingly engaged with the frame main body section. Namely, in the sensor of this invention, the folded-back section of the metallic terminal member is put in a plural support-point condition, i.e., supported at least at two points provided by the connection side end portion and the frame abutment portion.

The folded-back section in a condition of being supported at two or more points produces a larger stress when resiliently deformed, as compared with a case of one-point support condition, thus making it possible to press the metallic terminal member itself against the detection element with a larger stress and therefore attain a good electrical connection condition between the metallic terminal member and an electrode terminal member of the detection element.

In the meantime, since the stress produced by the metallic terminal member increases when the folded-back section is brought into a plural-point support condition, the metallic terminal member is not needed to be larger in the width side and thickness as compared with a prior art metallic terminal member in which a folded-back section is always put into a one-point support condition (cantilever condition, therefore can prevent the space for disposition thereof from increasing, and suited for use in the sensor that is required to be small-sized.

Further, in the above-described sensor, the metallic terminal member is preferably configured so that, when in a free condition before being electrically connected to the electrode terminal section of the detection element, the frame abutment portion of the folded-back section is not abuttingly engaged with the frame main body section, while on the other hand when the folded-back section is electrically connected to the electrode terminal section and resiliently deformed toward the frame main body section, the frame abutment portion is abuttingly engaged with the frame main body section.

In the sensor of the present invention, the metallic terminal member is configured so that, when in a free condition, the frame abutment portion of the folded-back section is not abuttingly engaged with the frame main body section to allow the folded-back section to be supported at one place (at the connection side end portion connected to the front end of the frame main body section) on the frame main body section. Due to this, the metallic terminal member is configured, when in a condition where the frame abutment portion of the folded-back section is not abuttingly engaged with the frame main body section, so as to be pressed against the electrode terminal section of the detection element by stress that is produced by resilient deformation of the connection side end portion and its adjacent portion of the folded-back section. When the folded-back section continues resilient deformation toward the frame main body section to abuttingly engage the frame abutment portion with the frame main body section, the folded-back section is supported at least at two places, i.e., at the connection side end portion and the frame abutment portion, on the frame main body section.

As described above, the metallic terminal member provided to the sensor of the present invention is configured so that the pressure that urges the metallic terminal member against the detection element varies depending upon whether or not the frame abutment portion of the element abutment section is abuttingly engaged with the frame main body section. More specifically, the metallic terminal member is configured so that the pressure that urges the metallic terminal member against the electrode terminal section of the detection element when the frame abutment portion of the element abutment section is abuttingly engaged with the frame main body section (two-point support condition) becomes larger as compared with that when the frame abutment portion of the element abutment section is not abuttingly engaged with the frame main body section (one-point support condition).

By this, in case of assembly of the metallic terminal member and the detection element in a sensor production process, the element abutment section of the metallic terminal member is pressed against the electrode terminal section of the detection element with a relatively smaller force in the first half of the assembly work, thus making it possible to inhibit an excessively large pressure from being applied to the detection element and causing breakage thereof. Further, after the assembly work is completed, the folded-back section is brought into the two-point support condition of being supported at the connection side end portion and the frame abutment portion upon the frame main body section. Since the stress caused by resilient deformation of the folded-back section in the two-point support condition is larger as compared with the case of the one-point support condition as described above, the electrical connection condition between the metallic terminal member and the electrode terminal member of the detection element can be good.

Further, in the above-described sensor, the folded-back section is preferably configured to extend from the front end of the frame main body section while changing the direction of extension, be disposed between the electrode terminal section of the detection element and the frame main body section and form the element abutment section for contact with the electrode terminal section.

In the sensor of this invention, the folded-back section of the metallic terminal member is disposed between the detection element and the frame main body section and constitutes an element abutment section for contact with an electrode terminal section. Namely, the folded-back section that is in a two-point support condition relative to the frame main body section is brought into contact with an electrode terminal section of the detection element. Due to this, it becomes possible to press the folded-back section against the electrode terminal section of the detection element with a larger stress, and it becomes possible to make the electrical connection condition between the metallic terminal member and the electrode terminal section of the detection element further better.

Further, in the above-described sensor, it is preferable that the folded-back section that constitutes the element abutment section protrudes toward the electrode terminal section of the detection element and its apex portion includes a convex part for contact with the electrode terminal section.

By making the folded-back section be formed with the convex part that protrudes toward the electrode terminal section and bringing the apex of the convex part into contact with the electrode terminal section, the contact pressure of the folded-back section relative to the electrode terminal section can be made higher. Accordingly, the contact between the folded-back section of the metallic terminal member and the electrode terminal section of the detection element can be assured, and the reliability of their electrical connection condition can be improved.

Further, in the above-described sensor, it is preferable that the folded-back section that constitutes the element abutment section is formed so as to have a width size that ranges from 0.5 mm to 2.0 mm.

The metallic terminal member with the folded-back section whose width size is set as described above can be electrically connected to each electrode terminal section separately, without being electrically connected to a plurality of electrode terminal sections even in case the electrode terminal section is small in the width size and the detection element is formed with a plurality of electrode terminal sections, and thus can form an electric path suitably. Further, the strength of the metallic terminal member can be maintained good, and the durability of the sensor can be good. Further, since the metallic terminal member can be disposed in a small disposition space, it becomes possible to form an electrical path in a small sensor and make the sensor small-sized.

In the meantime, the term "width size" is herein used to indicate the size in the direction perpendicular both to the axial direction and to the direction of an intervening space between the folded-back section and the frame main body section.

Further, in the above-described sensor, it is preferable that the sensor has a separator disposed radially outside of the rear end side of the detection element and made of an insulating material and the metallic terminal member is held in a condition of the folded-back section being resiliently deformed toward the frame main body section and between the detection element and the separator.

By holding the metallic terminal member in a condition of the folded-back section being resiliently deformed toward the frame main body section and between the detection element and the separator, the electrical connection condition between the metallic terminal member and the detection element can be attained assuredly. Thus, the sensor of the present invention can maintain the connection condition between the metallic terminal member and the electrode terminal section of the detection element stably for a long period of time even in case it is used under a condition of being attached to a vehicle or the like whose vibration is severe.

Further, in the above-described sensor, it is preferable that the frame abutment portion of the folded-back section is formed into a curved shape.

In the sensor of the present invention, the frame abutment portion of the folded-back section of the metallic terminal member is formed into a curved surface shape, and the frame abutment portion is abuttingly engaged with the frame main body section. Thus, even in the case the sensor of this invention is used under a condition of being attached to a vehicle or the like whose vibration is severe, it becomes possible to considerably reduce the degree to which metallic powder is produced due to rubbing between the frame abutment portion and the frame main body section. Accordingly, by the sensor of this invention, it becomes possible to effectively inhibit dispersing of metallic powder due to rubbing of the frame abutment portion and the frame main body section and bad influence on the connection condition between the metallic terminal member and the detection element even in the case the sensor is used under the condition of being attached to a vehicle or the like whose vibration is severe.

According to another aspect of the present invention, there is provided a method of producing a sensor including a detection element in the form of an axially extending plate, having a front end side to face an object to be measured and formed with an electrode terminal section at a rear end side, a separator disposed radially outside of a rear end side of the detection element formed with an electrode terminal section and made of an insulating material, and a metallic terminal member formed from a metallic sheet material and contacting the electrode terminal section thereby being electrically connected thereto to form an electrical path, wherein the metallic terminal member includes an axially extending frame main body section and a folded-back section extending while being bent to change the direction of extension, from a front end of the frame main body section axially toward a rear end side of the frame main body section and disposed between the electrode terminal section of the detection element and the frame main body section, wherein the folded-back section includes a connection side end portion connected to a front end of the frame main body section and a frame abutment portion formed at a position closer to a rear end than the connection side end portion for abutting engagement with the frame main body section, and wherein the metallic terminal member is configured so that the frame abutment portion of the folded-back section is not abuttingly engaged with the frame main body section when the metallic terminal member is in a condition before being electrically connected to the electrode terminal section of the detection element and the folded-back section is abuttingly engaged with the frame main body section when the metallic terminal member is electrically connected to the electrode terminal section to cause the folded-back section to resiliently deform toward the frame main body section, the method comprising a first step of disposing the metallic terminal member in the separator, a second step of pressing the detection element against the folded-back section thereby resiliently deforming the folded-back section toward the frame main body section and bringing a frame contact portion of the folded-back section into contact with the frame main body section, and a third step of changing relative positions of the detection element and the separator in a way as to allow the separator to be disposed radially outside the detection element.

By the sensor according to the present invention, breakage of the detection element at the assembly work for assembling the detection element and the metallic terminal member during the sensor production process is hard to be caused, thus making it possible to improve the production efficiency of the sensor.

Further, even in the structure where the space for disposition of the metallic terminal member is small, a sensor in which the electrical connection condition between the electrode terminal section of the detection element and the metallic terminal member is good can be attained efficiently.

DETAILED DESCRIPTION OF THE INVENTION

An embodiment of the present invention will be described hereinafter by reference to drawings.

In the meantime, according to this embodiment will be described a kind of gas sensor, specifically a wide-range air/fuel ratio sensor 2 (hereinafter also referred to as air/fuel ratio sensor 2) composed of a detection element (gas sensor element) for detecting a particular gas which is an object to be measured and contained in an exhaust gas, for use in an air/fuel ratio feedback control in automotive or other various kinds of internal combustion engines.

Figure 1:
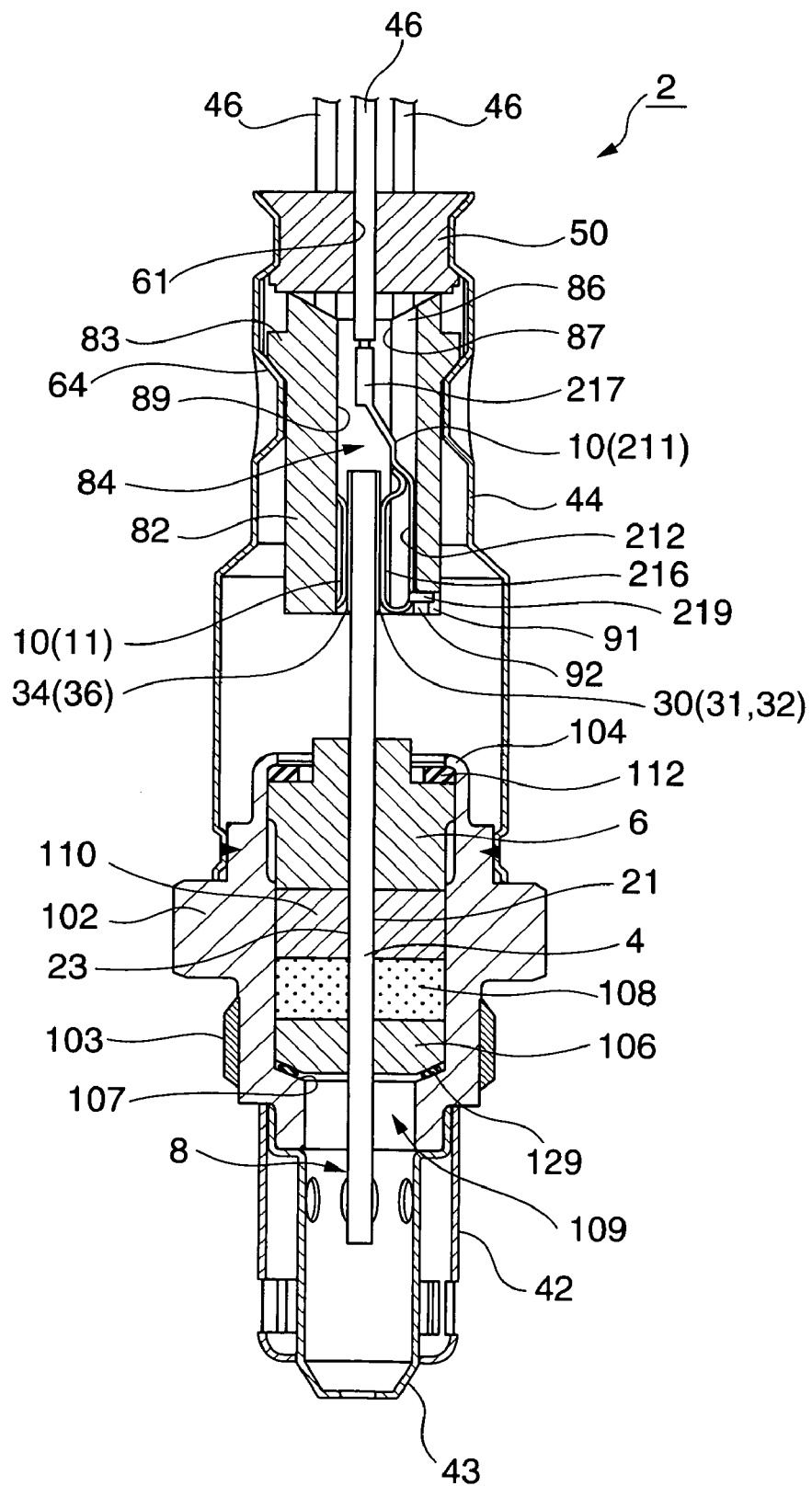
FIG. 1 is a sectional view showing an overall structure of a wide-range air/fuel ratio sensor according to an embodiment.

FIG. 1 is a sectional view showing an overall structure of the air/fuel ratio sensor 2 according to an embodiment of the present invention.

The air/fuel ratio sensor 2 includes a detection element 4 in the form of a plate extending in an axial direction (up and down direction in the drawing), a tubular metallic housing 102 accommodating the detection element 4 in a way as to allow a front end portion of the detection element 4 to protrude therefrom, a ceramic sleeve 6 disposed between the detection element 4 and the metallic housing 4, and a separator 82 made of alumina and disposed in a way as to surround a rear end portion of the detection element 4.

Figure 2:
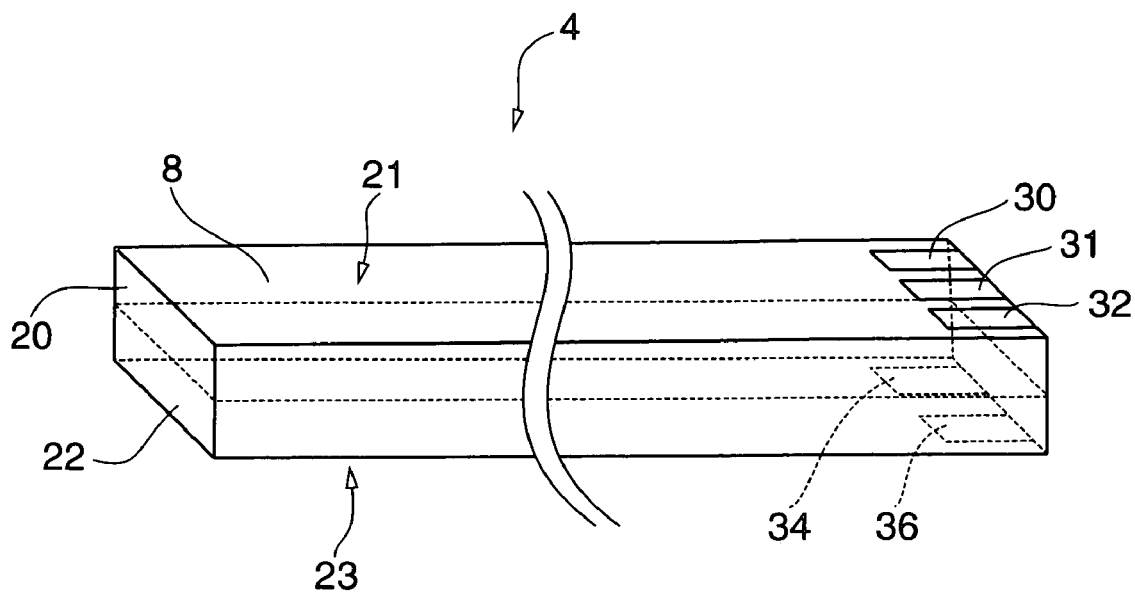
FIG. 2 is a perspective view depicting a schematic structure of a detection element.

The detection element 4 is in the form of an axially extending plate and formed at a front end side (lower side in the figure) to face a gas that is an object to be measured, with a detection section 8 covered by a protection layer and at a first plate surface 21 and a second plate surface 23 of outer surfaces of a rear end side (upper side in the figure), which first and second plate surfaces have a relation between a front side and a rear side, with electrode terminal sections 30, 31, 32, 34 and 36 (refer to FIG. 2). Five lead frames (metallic terminal members) 10 are disposed between the detection element 4 and the separator 82 and electrically connected to the electrode terminal sections 30, 31, 32, 34 and 36, respectively. Further, the lead frames 10 are electrically connected at the rear end sides thereof to lead wires 46 that are disposed inside the sensor through movement from the outside and constitute electrical paths for current flowing between an external circuit to which the lead wires 46 are connected and the electrode terminal sections 30, 31, 32, 34 and 36.

The metallic housing 102 has at an outside surface a threaded section 103 for fixation to an exhaust pipe and is formed into a nearly tubular shape having inside thereof a through hole extending axially therethrough. Further, the metallic housing 102 is configured so as to hold the detection element 4 within the through hold 109 in a way as to allow the detection section 8 to protrude from the front end side while allowing the electrode terminal sections 30, 31, 32, 34 and 36 to protrude from the rear end side.

To the front end side (lower side in FIG. 1) outer periphery of the metallic housing 102 is attached by welding or the like an outer protector 42 and inner protector 43 which are made of metal (for example, stainless steel or the like) to constitute a dual-wall and have a plurality of holes.

Further, a separator 82 is disposed around the rear end side (upper side in FIG. 1) of the detection element 4, which protrudes from a rear end portion 104 of the metallic housing 102 and accommodates the electrode terminal sections 30, 31, 32, 34 and 36 within an insertion hole 84.

To the rear end side outer periphery of the metallic housing 102 is fixedly attached an outer tube 44. At the rear end side (upper side in FIG. 1) opening portion of the outer tube 44 is disposed a grommet 50, and lead wires 46 are inserted into lead wire insertion holes 61 of the grommet 50.

The separator 82 has a flange portion 83 protruding radially outward from an external surface thereof and is disposed inside the outer tube 44 by being abuttingly engaging at the flange portion 83 with an outer tube side support portion 64 of the outer tube 44.

In the meantime, within a through hole 109 of the metallic housing 102 are placed one upon another an annular ceramic holder 106, a power filling layer 108 (hereinafter also referred to as talcum ring 108), an auxiliary sleeve 110 and a ceramic sleeve 6 in this order from the front end side to the rear end side in a way as to surround the circumferential periphery of the detection element 4. These laminated layers are fixedly held between a shoulder portion 107 and a rear end portion 104 by caulking by way of packing 129 and a caulking ring 112.

In this connection, a perspective view of the schematic structure of the detection element 4 is shown in FIG. 2. In the meantime, in FIG. 2, an axially intermediate portion of the detection element 4 is omitted.

The detection element 4 includes an element section 20 formed into an axially (in the horizontal direction in FIG. 2) extending plate shape and a heater 22 formed into a similar axially extending plate shape extending, which are placed one upon another to allow the detection element to be formed into a plate shape having a rectangular cross section. In the meantime, since the detection element 4 used as the air/fuel ratio sensor 2 is of the type known in the art, the detailed description of the inside structure, etc. are omitted but the schematic structure thereof is as follows.

First, the element section 20 consists of an oxygen concentration cell including porous electrodes formed on the opposite sides of a solid electrolytic substrate, an oxygen pump cell including porous electrodes similarly formed on the opposite sides of a solid electrolytic substrate, and a spacer placed between the cells for forming a hollow gas measurement chamber. The solid electrolytic substrate is made of a solid solution of zirconia and yttria as a stabilizer, and the porous electrode is made of a material containing Pt as a major component. Further, the spacer that forms the gas measurement chamber is made of a material containing alumina as a major component, and one of the porous electrodes of the oxygen concentration cell and one of the porous electrodes of the oxygen pump cell are disposed so as to be exposed to the hollow measurement gas chamber. In the meantime, the measurement gas chamber is formed so as to be positioned at the front end side of the element section 20, and a portion of the element section, at which the measurement gas chamber is formed, corresponds to the detection section 8.

Then, the heater 22 is formed so as to have a heating resistor pattern that is made of a material containing Pt as a major component and interposed between insulating substrates made of alumina as a major component.

The element section 20 and the heater 22 are connected to each other by interposing therebetween a ceramic layer (e.g., zirconia system ceramic or alumina system ceramic). Further, on at least the surface of the electrodes of the detection element 4, which is exposed to an object to be measured (in this embodiment, exhaust gas) is formed a protection layer (not shown) made of porous ceramic for protection from poisoning. In the meantime, in this embodiment, the protection layer covers all the front end side surface of the detection element, which includes the surface of the electrode to be exposed to the exhaust gas.

Such a detection element 4, as shown in FIG. 2, is formed with three electrode terminal sections 31, 32, 33 at the rear end side (the right-hand side in FIG. 2) of the first plate surface 21 and two electrode terminal sections 34, 36 at the rear end side of the second plate surface 23. The electrode terminal sections 30, 31, 32 are formed at the element section 20, one of which electrode terminal sections is electrically connected, in the manner of common use, to one of the porous electrodes of the oxygen concentration cell that is exposed to the inside of the measurement gas chamber and one of the porous electrodes of the oxygen pump cell. Further, remaining two of the terminal electrodes 30, 31, 32 are electrically connected to the other of the porous electrodes of the oxygen concentration cell and the other of the porous electrodes of the oxygen pump cell. Further, the electrode terminal sections 34, 36 are formed at the heater 22 and connected to the opposite ends of the heating resistor pattern by way of a via (not shown) extending crosswise in the thickness direction of the heater 22, respectively.

Figure 3:
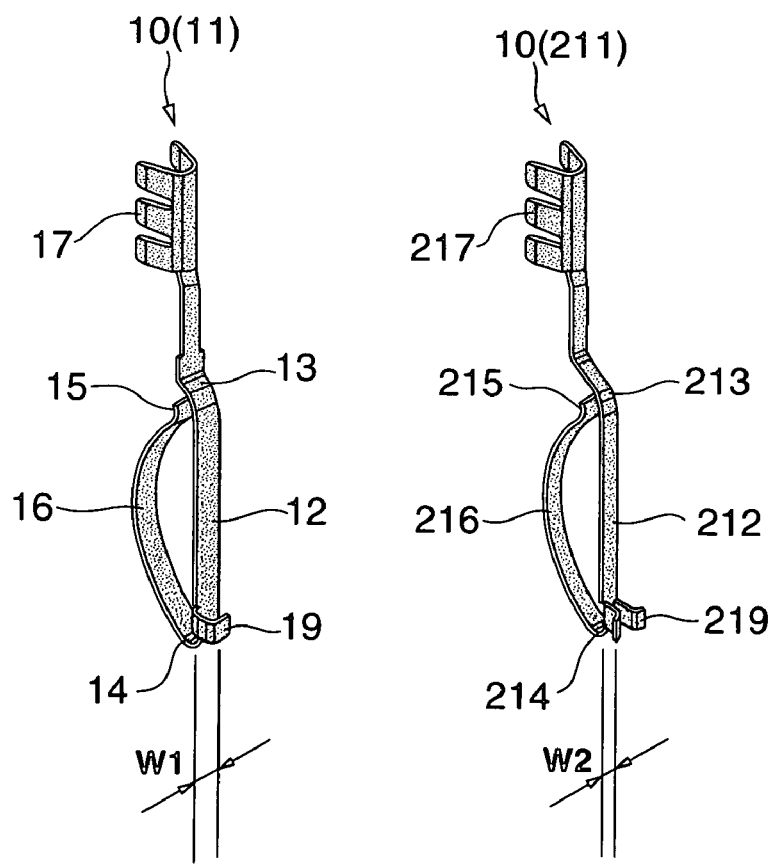
FIG. 3 is a perspective view depicting an external appearance of a lead frame.

Then, the lead frame 10 will be described. FIG. 3 is a perspective view showing the external appearance of the lead frame 10. In the meantime, the air/fuel ratio sensor 2 of this embodiment is configured to include two kinds of lead frames 10 that are different in the shape of the frame locking section (the first lead frame 11 on the left-hand side of FIG. 3 and the second lead frame 211 on the right-hand). Further, the lead frame 10 is made of a known material (e.g., inconel, stainless steel or the like) that can maintain the resiliency (springing resilience) even when exposed to a high temperature repeatedly.

First, the first lead frame 11 includes a frame main body section 12 formed from an axially extending plate, an element abutment section 16 extending while being bent, from a front end of the frame main body section 12 so as to be disposed between the frame main body section 12 and the detection element 4 and having a portion at which it is abuttingly engaged with the electrode terminal section of the detection element 4, and a lead wire connection section 17 electrically connected with a lead wire 46.

The frame main body section 12 has nearly at an axially central position a curved portion 13 and is configured so that a front end side portion closer to the front end than the curved portion 13 and a rear end side portion closer to the rear end than the curved portion 13 are different in the position with respect the plate surface thickness direction. The surface of the curved portion 13, that faces the frame abutment portion 15 constitutes an inclined surface that faces the front end side and has a function of inhibiting the frame abutment portion 15 from moving axially toward the rear end side or radially outward at the time of abutting engagement with the frame abutment portion. Further, the frame main body section 12 is formed so as to be 1.1 mm in the width size W1 and 0.2 mm in the thickness at the plate surface of the front end side portion closer to the front end than the central position.

In the meantime, the first lead frame 11 includes a first frame locking section 19 for engagement with the separator 82 at the front end side of the frame main body section 12. The first frame locking section 19 is extended from a side surface of a front end side portion of the frame main body section 12 in the direction perpendicular to the plate surface and bent so as to have a portion parallel with the plate surface of the frame main body section 12.

The element abutment section (folded-back section) 16 is configured so as to extend while being bent radially inward to change the direction of extension, from a front end of the frame main body section 12 axially toward the rear end side. The element abutment section 16 includes a connection side end portion 14 connected to the front end of the frame main body section 12 and a frame abutment portion 15 that is positioned closer to the rear end than the connection side end portion 14 and put in a condition of being spaced apart from the frame main body section 12 when the first lead frame 11 itself is in a free condition.

Herein, the element abutment section 16 is formed so as to be 1.1 mm in the width side of the plate surface and 0.2 mm in the thickness. Further, element abutment section 16 is formed into a circular arc shape and curved so that the distance between the axially central portion and the frame main body section 12 is larger as compared with that between the frame abutment portion 15 and the frame main body section 12 and a convex side curved surface of the circular arc shape is abuttingly engaged with the detection element 4.

In the meantime, when an external force is applied to the element abutment section 16 (specifically, an external force from the element abutment section 16 toward the frame main body section 12 is applied), the frame abutment portion 15 is resiliently deformed toward the frame main body section 12, and finally the frame abutment portion 15 is abuttingly engaged with the curved portion 13 of the frame main body section 12.

Further, the first lead frame 11 is configured so that when there is no external force applied thereto and the connection side end section 14 (the element abutment section itself) is not resiliently deformed, the distance between the abutment portion 15 of the element abutment section 16 and the main frame section 12 is smaller than the depth of the first frame disposition groove 86 and the second frame disposition groove 88 of the separator 82.

In the meantime, the first lead frame 11 is configured so that in case the element abutment section 16 in a condition of being resiliently deformed toward the frame main body section 12 is held between the detection element 4 and the separator 82, the abutment portion 15 of the element abutment section 16 is brought into contact with the curved portion 13 of the frame main body section 12 and at least a portion of the element abutment section 16 protrudes from the first frame disposition groove 86 and the second frame disposition groove 88 to contact an electrode terminal section of the detection element 4.

Then, the second lead frame 211 will be described.

The second lead frame main body section 212 is formed so that a front end side portion closer to the front end than a portion around a curved portion 213 is 0.8 mm in the plate surface width W2 and 0.2 mm in the plate thickness and substantially similar in the sectional shape with respect to a plane parallel to the axial direction and perpendicular to the plate surface, to the frame main body section 12 though different in the width of a lateral surface from the frame main body section 12 of the first lead frame 11.

The second element abutment section 216 is formed so as to be 0.8 mm in the plate surface width W2 and 0.2 mm in the plate thickness and substantially similar in the circular arc sectional shape with respect to a plane parallel to the axial direction, to the element abutment section 16, and has a second connection side end portion 214 corresponding to the connection side end portion 14 and a second frame abutment portion 215 corresponding to the frame abutment portion 15.

Further, the second lead frame 211 has at a portion of the second frame main body section 212 two second frame locking sections 219 that can be disposed in the second locking grooves 91 of the separator 82. The second locking sections 219 are configured so as to extend from the second main body section 212 in the direction perpendicular to the plate surface thereof and be bent outward to have portions parallel to the plate surface of the second frame main body section 212.

Further, the second lead frame 211 has at the rear end of the second lead frame main body section 212, a second lead wire connection section 217 which is formed into a similar shape to the lead wire connection section 17 of the first lead frame 11.

Of the lead frames 10 configured in this manner, the four first lead frames 11 and one second lead frame 211 are inserted into the insertion hole 84 of the separator 82 so as to be put in a condition of being insulated from each other.

In this instance, the four first lead frames 11 are disposed in the two first frame disposition grooves 86 corresponding to the electrode terminal sections 30, 32 of the detection element 4 and in the two frame disposition grooves 88 corresponding to the two second frame disposition grooves 88 corresponding to the electrode terminal sections 34, 36. The second lead frame 211 is disposed in the first frame disposition groove 86 corresponding to the electrode terminal section 31 of the detection element 4.

Then, the separator 82 will be described.

Figure 4:
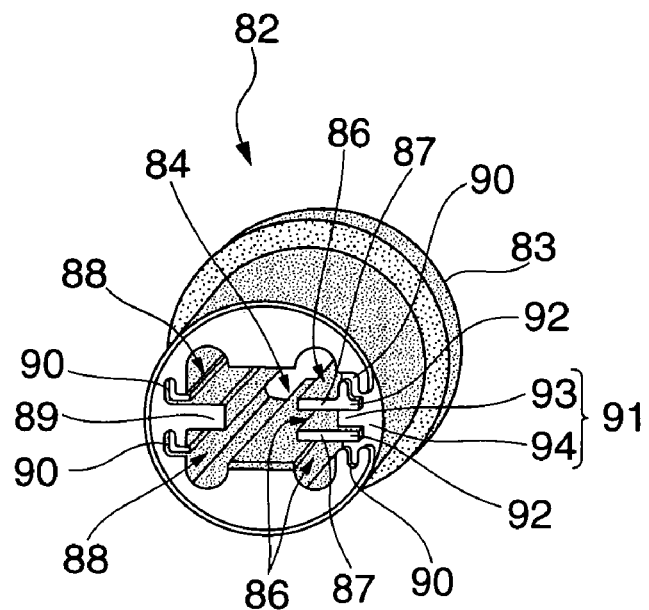
FIG. 4 is a perspective view of an external appearance of a separator.

FIG. 4 is a perspective view showing the external appearance of the separator 82 when observed from the front end side thereof. As shown in FIG. 4, at the inner wall surface of the insertion hole 84, which faces the first plate surface 21 (not shown), are provided three first frame disposition grooves 86 for disposing three lead frames 10 in a condition of being electrically insulated from each other, and first rib portions 87 that form boundaries of the first frame disposition grooves 86.

Further, at the inner wall surface of the insertion hole 84, which faces the second plate surface 23 (not shown) of the detection element 4, are formed two second frame disposition grooves 88 for disposing the two lead frames 10 in a condition of being electrically insulated from each other and a second rib portion 89 that forms a boundary of the second frame disposition grooves 88. In the meantime, the second disposition grooves 88 are formed at the second plate surface 23 of the detection element 4 and at the positions corresponding to the electrode terminal sections 34, 36.

The first rib portions 87 and second rib portion 89 have a function of preventing the lead frames 10 disposed in the adjacent frame disposition grooves from contacting each other and thereby preventing the electrical path from becoming defective.

Further, the separator 82 has at the front end surface thereof (this side surface in the figure) first locking grooves 90 and a second locking groove 91 that are formed so as to be joined to the front end side opening portion of the insertion hole 84.

The first locking grooves 90 are formed into a nearly L-shape when observed from the front end side and configured so as to dispose therewithin a first frame locking section 19 of the lead frame 10, which will be described later. In the meantime, the first locking grooves 90 are formed so as to connected thereto two of the three first frame disposition grooves 86, which are formed at the opposite sides and the second frame disposition grooves 88.

The second locking groove 91 consists of a narrower groove portion 93 formed between two protrusion portions 92 and a wider groove portion 94 formed at a portion of the insulation contact member 82, which is positioned at a radially outer side of the narrower groove portion 93, and is configured so as to dispose therewithin the second frame locking sections 219 of the lead frame 10, which will be described later. In the meantime, the protrusion portion 92 is formed so as to be continuous from an end of the first rib portion 87. Further, the second locking groove 91 is formed at one place where it is connected to one first frame disposition groove 86 that is formed in the middle of the three first frame disposition grooves 86.

The lead frame 10 is disposed in the insertion hole 84 through insertion into the insertion hole 84 of the separator together with the lead wire 46 after the lead wire 46 is connected to the lead wire connection section 17 (second lead wire connection section 217).

Figure 5:
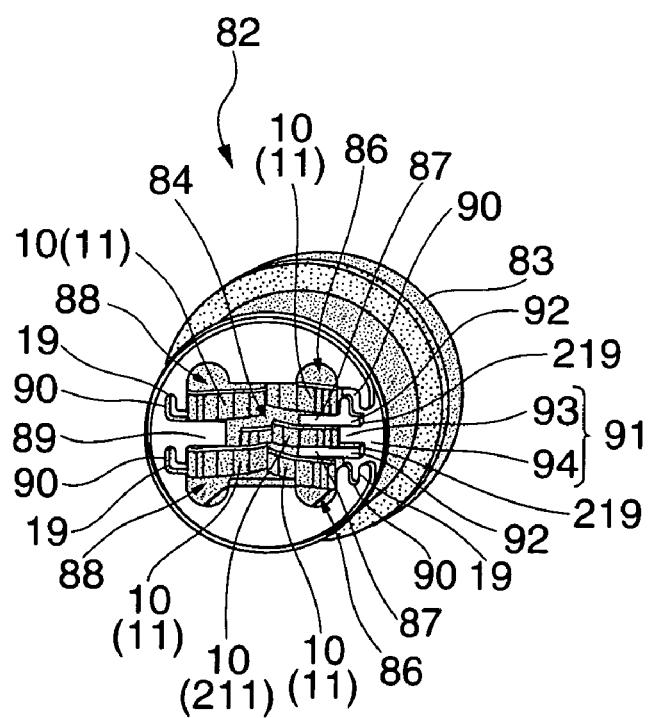
FIG. 5 is a perspective view of a separator in a state where a lead frame is disposed in an insertion hole.

FIG. 5 is a perspective view of the separator 82 insertion hole 84 in the condition in which the lead frame 10 is inserted into the insertion hole 84. As shown in FIG. 5, the first frame locking section 19 of the first lead frame 11 is disposed in the first locking groove 90 of the separator 82, and the second frame locking section 219 of the second lead frame 211 is disposed in the second locking groove 91 of the separator 84.

By inserting the detection element 4 into the contact insertion hole 84 of the separator 84 in a condition of disposing therein the lead frames 10 as described above, the element abutment section 16 (second element abutment section 216) can be abuttingly engaged and electrically connected with one of the electrode terminal sections 30, 31, 32, 34, 36 of the detection element 4.

Then, the assembly work for inserting the detection element 4 into the insertion hole 84 in a condition of disposing therein the lead frames 10 thereby assembling the detecting element 4, the lead frame 10 and the separator 82 into a unit will be described.

Figure 6:
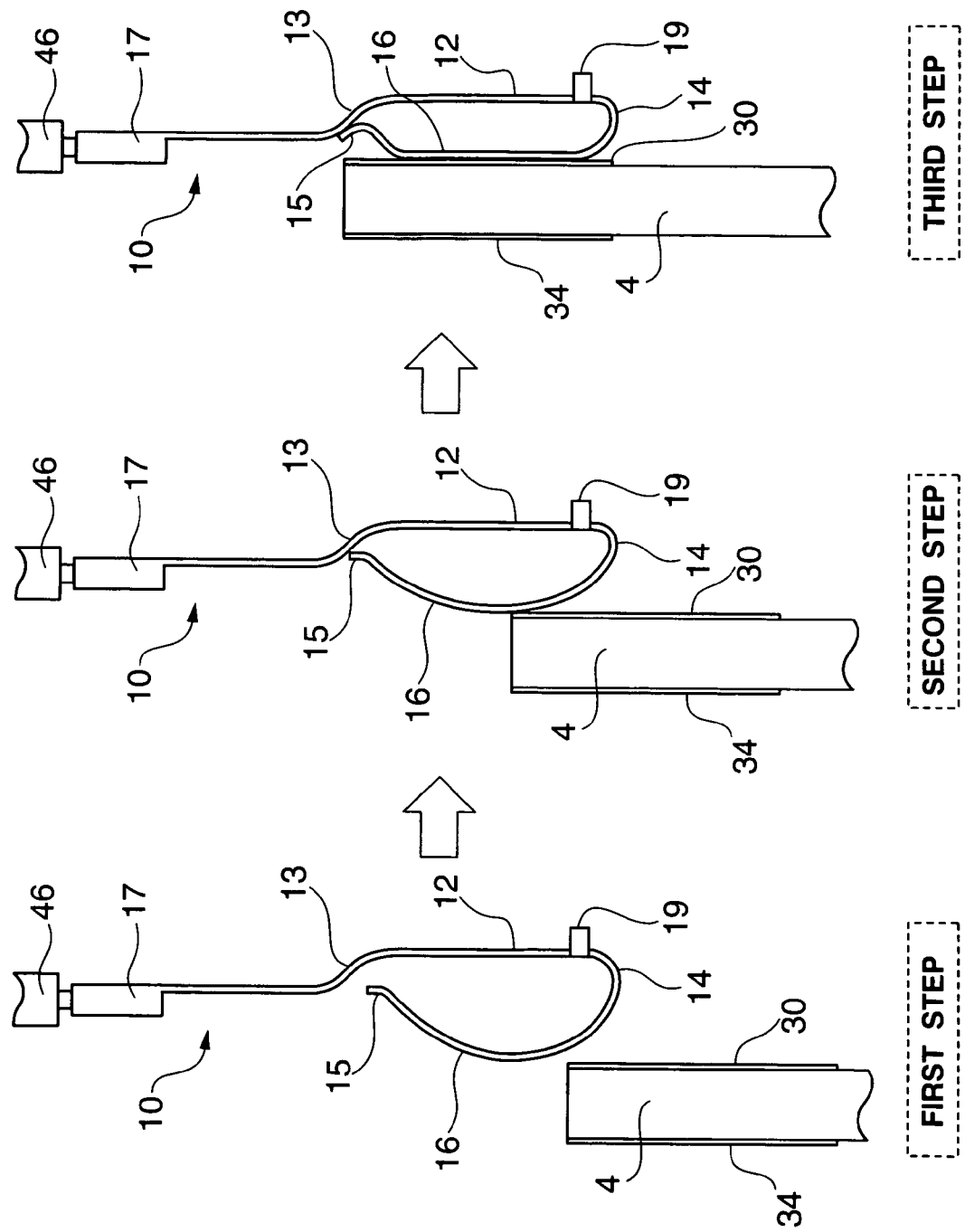
FIG. 6 is a view for illustrating states of deformation of the lead frame within the insertion hole at the time of a work for inserting the detection element into the separator.

FIG. 6 illustrates the states of deformation of the lead frame 10 within the insertion hole 84 during the work for inserting the detection element 4 into the insertion hole 84 of the separator 82. In the meantime, in FIG. 6, one lead frame 10 and the detection element 4 are shown and the separator 82 is omitted for brevity.

First, at the first step immediately after the beginning of the assembly work, the detection element 4 is disposed at the front end side of the separator 82 and thereafter the detection element 4 is moved to the front end side opening portion of the insertion hole 84 while at the same time the detection element 4 is abuttingly engaged with the element abutment section 16 of the lead frame 10. By pressing the detection element 4 against the element abutment section 16 of the lead frame 10 thereby applying thereto an external force, the connection side end portion 14 is resiliently deformed (in other words, the element abutment section 16 is resiliently deformed toward the frame main body section 12), while at the same time a work for causing the frame abutment portion 15 of the element abutment section 16 to go closer to the curved portion 13 of the frame main body section 12 is performed.

Then, in the second step, a work for pushing the detection element 4 against the element abutment section 16 thereby resiliently deforming the element abutment section 16 against the frame main body section 12 and abuttingly engaging the frame abutment portion 15 of the element abutment section 16 with the frame main body section 12 (the curved portion 13 of the frame main body section 12). By this, the element abutment section 16 is put into a condition of being supported at two places, i.e., at the connection side end portion 14 and the frame abutment portion 15, i.e., put in a two-point support condition.

At the next third step, a work for inserting the detection element 4 further into the rear end side of the insertion hole 84 and changing the relative positions of the detection element 4 and the separator 82 is performed so as to cause the inner wall surface of the insertion hole 84 of the separator 82 to face the electrode terminal sections 30, 31, 32 and 34 of the detection element 4. By this, the front end side portion of the frame main body section 12 and the element abutment section 16 of the lead frame 10 are put into the condition of being placed between the detection element 4 and the inner wall surface of the insertion hole 84 (refer to FIG. 1). In this instance, the element abutment section 16 is resiliently deformed so as to allow the axially central portion thereof to extend along the plate surface of the detection element 4 and therefore put into a condition of being abuttingly engaged at a wide area with the electrode terminal section of the detection element 4.

By performing the assembly work in the above-described manner, the detection element 4, the lead frame 10 and the separator 82 can be assembled into a unit. While the resilient deformations of the first lead frame 11 at the time of assembly work have been herein described, the second lead frame 211 exhibits a deformation condition similar to the first lead frame 11.

Figure 7:
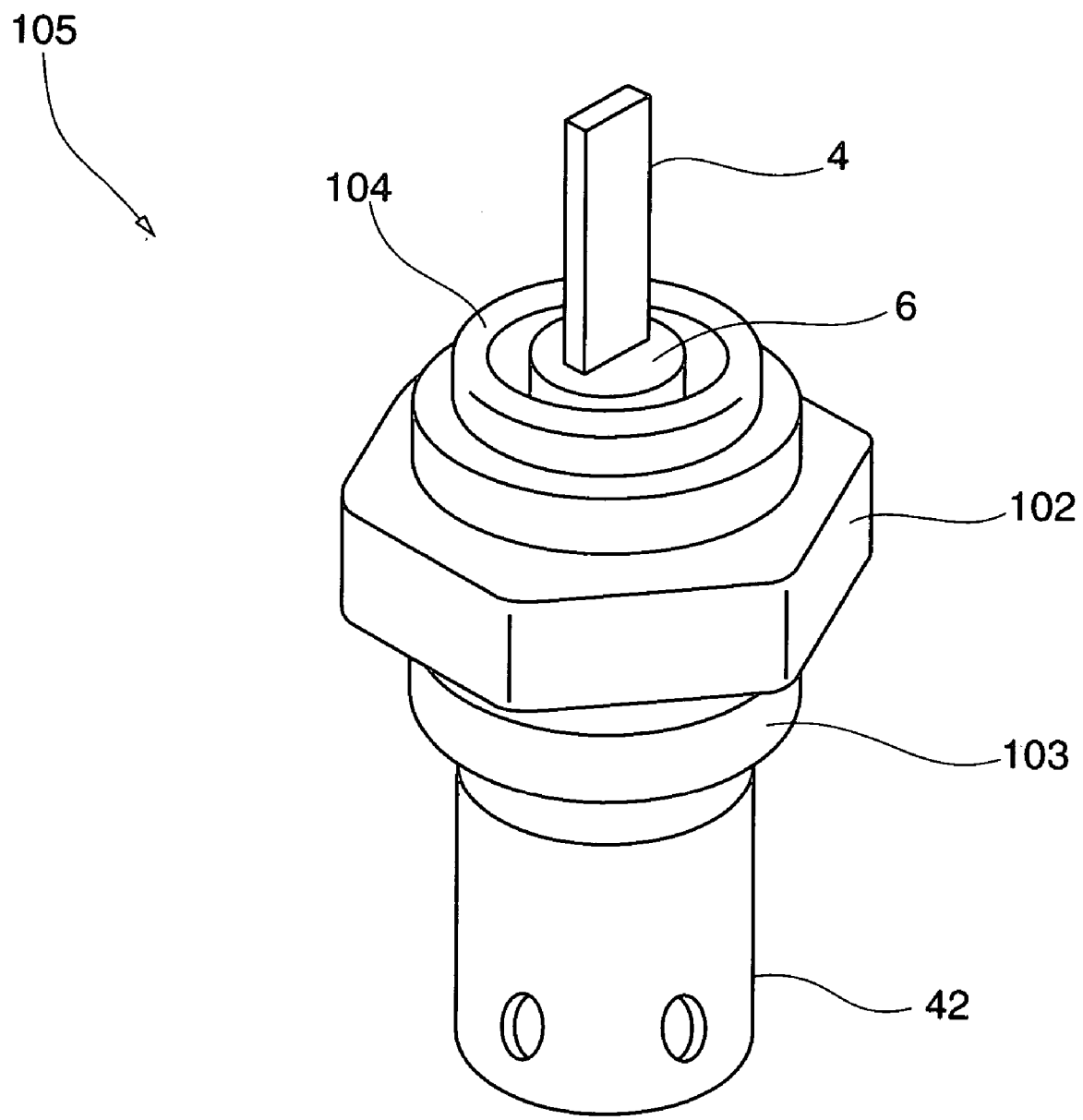
FIG. 7 is a perspective view of an intermediate assembly in a state where a rear end side of the detection element is protruded from a rear end portion of a metallic member and a rear end portion of a ceramic sleeve.

In the meantime, the assembly work for assembling the detection element 4, the lead frame 10 and the separator 82 into an integral unit is executed in the middle of a production process of the air/fuel ratio sensor 2. In the production process of the air/fuel ratio sensor 2, it is executed in the stage prior to the assembly work, a work for assembling an intermediate assembly part consisting of the detection element 4, the ceramic sleeve 6, the talcum ring 108, the ceramic holder 106, the metallic housing 102, etc. FIG. 7 is a perspective view of the intermediate assembly part 105 in a condition where the rear end side of the detection element 4 protrudes from the rear end portion 104 of the metallic housing 102 and the rear end portion of the ceramic sleeve 6.

In the production process of the air/fuel ratio sensor 2, the lead frame 10 and the separator 82 can be attached to the detection element 4 by performing the above-described assembly work on the detection element 4 in the condition of constituting the intermediate assembly part 105.

By executing, after the separator 82 and the detection element are assembled together, a fixing work, etc. for joining the outer tube 4, etc. to the metallic housing 102 by laser welding or the like and fixing the grommet 50 to the outer tube 44 by caulking, the air/fuel ratio sensor 2 is completed and the production process of the air/fuel ratio sensor 2 is finished.

In the meantime, in this embodiment, the lead frame 10 corresponds to the metallic terminal member described in "what is claimed is", and the element abutment section 16 and the second element abutment section 216 correspond to the folded-back section. Further, of the sensor production process, the working step for disposing the lead frame 10 within the contact insertion hole 84 of the separator 82 corresponds to the first step described in "what is claimed is", the first step and the second step in the assembly work for assembling the lead frame 10 and the separator 82 together corresponds to the second step described in "what is claimed is", and the third step in the assembly work corresponds to the third step described in "what is claimed is".

As having been described as above, the air/fuel ratio sensor 2 of this embodiment is constructed to use the lead frame 10 (first lead frame 11, second lead frame 211) which is configured so that the support condition of the element abutment section 16 (second element abutment section 216) which is brought into contact with the electrode terminal section of the detection element 4 varies from the one-point support condition to the two-point support condition.

The lead frame 10 in a condition where the frame abutment portion 15 (second frame abutment portion 215) of the element abutment section 16 is not engaged with the frame main body section 12 (second frame main body section 212), i.e., in the one-point support condition is configured so as to push the element abutment section 16 against the electrode terminal section of the detection element 4 with a small stress caused by resilient deformation of the connection side end portion 14 (second connection side end portion 214) and its adjacent portion. Further, in case the element abutment section 16 (second element abutment section 216) is resiliently deformed toward the frame main body section 12 (second frame main body section 212) to cause the frame abutment portion 15 (second frame abutment portion 215) to abuttingly engage the frame main body section 12 (second frame main body section 212), the lead frame 10 produces a large stress due to resilient deformation of the axially central portion of the element abutment section 16 (second element abutment section 216).

Namely, the lead frame 10 is configured to produce a larger pressure (in other words, contact pressure) for pressing the element abutment section 16 (second element abutment section 216) against the detection element 4 when in the two-point support condition where the frame abutment portion 15 (second frame abutment portion 215) of the element abutment section 16 (second element abutment section 216) is abuttingly engaged with the frame main body section 12 (second frame main body section 212) than when in the one-point support condition where the frame abutment portion 15 (second frame abutment portion 215) of the element abutment section 16 (second element abutment section 216) is not abuttingly engaged with the frame main body section 12 (second frame main body section 212).

By this, at the time of assembling the lead frames 10 and the detection element 4 together in the production process of the air/fuel ratio sensor 2, the element abutment sections 16 (second element abutment sections 216) of the lead frames 10 are pressed against the electrode terminal sections 30, 31, 32, 34, 36 with a relatively smaller force in the first half stage of the assembly work. As a result, at the time of the assembly work for assembling the lead frames 10 and the detection element 4, it becomes possible to prevent an excessively large pressure from being caused by resilient deformation of the lead frame 10 and applied to the detection element 4, and it becomes possible to inhibit the detection element 4 from being broken by application of pressure.

Further, after the assembly work is completed, the element abutment section 16 (second element abutment section 216) is brought into the two-point support condition of being supported at the connection side end portion 14 (second connection side end portion 214) and the frame abutment portion 15 (second frame abutment portion 215) upon the frame main body section 12 (second frame main body section 212). By a large stress (resilient force) caused by resilient deformation of the element abutment section 16 (second element abutment section 216) in the two-point support condition, the element abutment section 16 (second element abutment section 216) itself of the lead frame 10 is pressed against the electrode terminal section of the detection element 4, thus making good the electrical connection condition between the lead frame 10 and the detection element 4.

For this reason, it is unnecessary to make the lead frame 10 larger in the width and thickness for the purpose of attaining a large resilient force and thereby making good the connection condition between the lead frame 10 and the detection element 4. Namely, as compared with a lead frame having an element abutment section in a one-point support condition, the lead frame 10 of this embodiment has an advantage of being able to be smaller in the width and thickness for producing an equal resilient force.

Accordingly, since the lead frame 10 produces a larger stress when the support condition of the element abutment section 16 (second element abutment section 216) changes from the one-point support condition to the two-point support condition, it can be smaller in the width size and the thickness as compared with the prior art lead frame (metallic terminal member) if it is required to produce the same resilient force. For this reason, the lead frame 10 of this embodiment makes it possible to inhibit increase in the disposition space and can be used suitably in the sensor that is required to be small-sized.

Further, since the air/fuel ratio sensor 2 is constituted by using the separator 82 formed with the first frame disposition groove 86 and the second frame disposition groove 88, the work for setting the disposed position (relative position) of the lead frame 10 relative to the separator 82 can be easier and the difficulty in the assembly work can be reduced. Further, by disposing the lead frame 10 in the first frame disposition groove 86 and the second frame disposition groove 88, it becomes possible to prevent the disposed position of the lead frame 10 from being varied in actual use of the air/fuel ratio sensor 2. For example, even in the case the outer tube 44 is deformed by an impact from the outside to exert an influence of deformation on the lead frame 10, it becomes possible to prevent the adjacent lead frames 10 from being brought into contact with each other and maintain the electrical path in a suitable condition.

Further, the lead frame 10 is configured so that even in the case the frame abutment portion 15 (second frame abutment portion 215) of the element abutment section 16 (second element abutment section 216) is abuttingly engaged with the frame main body section 12 (second frame main body section 212), the element abutment section 16 and the second element abutment section 216 are partially disposed outside of the first frame disposition groove 86 and the second frame disposition groove 88 of the inside of the insertion hole 84. Due to this, the element abutment section 16 and the second element abutment section 216 are never entirely disposed inside the first frame disposition groove 86 and the second frame disposition groove 88, thus making it possible to prevent occurrence of such a case where the lead frame 10 cannot be connected to the electrode terminal section.

Further, the lead frame 10, when in a free condition, is configured so that the distance between the element abutment section 16 (second element abutment section 216) and the frame main body section 12 (second frame main body section 212) is smaller than the depth of the first frame disposition groove 86 and the second frame disposition groove 88 of the separator 82. Due to this, in case the frame main body section 12 (second frame main body section 212) is abuttingly engaged with the bottom of the first frame disposition groove 86 and the bottom of the second disposition groove 88, the frame main body section 12 and the second frame main body section 212 are accommodated inside the frame disposition groove 86 and the second frame disposition groove 88.

For this reason, when the lead frame 10 is joined with the detection element 4 after being disposed in the separator 82, it becomes possible to prevent the frame abutment portion 15 (second frame abutment portion 215) from being lockingly engaged with a portion-around-opening (first rib portion 87) of the first frame disposition groove 86 or a portion-around-opening (second rib portion 89) of the second frame disposition groove 88, thus making it possible to abuttingly engage the frame abutment portion 15 (second frame abutment portion 215) with the frame main body section 12 (second frame main body section 215) assuredly.

By this, the frame abutment portion 15 (second frame abutment portion 215) of the element abutment section 16 (second element abutment section 216) is in a condition of being lockingly engaged with the first rib portion 87 or the second rib portion 89, such that it becomes possible to prevent the lead frame 10 from being deformed into an unsuitable shape at the work for assembly with the detection element 4.

Further, the lead frame 10 includes the first frame locking section 19 and the second frame locking section 219, and when the lead frame is disposed in the insertion hole 84 of the separator 82, the first frame locking section 19 and the second frame locking section 219 are disposed in the first frame locking groove 90 and the second frame locking groove 91 of the separator 82. By this, at the time of insertion of the detection element 4 into the insertion hole 84, it becomes possible to prevent the lead frame 10 from moving away from the inner wall surface of the insertion hole 84 and thereby prevent the lead frame 10 from being deformed into an unsuitable shape to deteriorate the condition of connection with the electrode terminal section of the detection element 4.

As a result, at the time of assembly of the detection element 4, the lead frame 10 and the separator 82, unsuitable deformation and breakage of the lead frame 10 is hard to be caused, thus making it possible to reduce the frequency of occurrence of defective at the work for production of the sensor and improve the production efficiency of the sensor.

While the embodiments of the present invention have been described as above, the present invention is not limited to the embodiments described as above but can otherwise be embodied variously.

For example, the separator that cooperates with the detection element to hold therebetween the metallic terminal member (lead frame) is not limited to the one-piece structure like the separator 82 that is formed from one-piece material but can be a divided type constituted by a plurality of members. There can be enumerated, as an example, such a divided type structure including a first insulation member that faces a front side plate surface of a detection element, a second insulation member that faces a rear side plate surface of the detection element and a holding and fixing member that holds the first insulation member and the second insulation member.

In the sensor using such a divided type separator, a resilient force for realizing a good electrical connection condition by the use of a lead frame whose element abutment section (folded-back section) can be put in a one-point support condition and a two-point support condition. By this, when the resilient force produced by the lead frame is set at a predetermined magnitude, the space for disposition of the lead frame can be smaller as compared with that according to the prior art and the sensor can be smaller in size.

Further, the sensor to which the present invention is applied is not limited to a sensor formed with the five electrode terminal sections but the present invention can be applied to a sensor having an detection element with four electrode terminal sections or less or six electrode terminal sections or more.

In the meantime, while in the above-described embodiment, two kinds of lead frames (first lead frame 11 and second lead frame 211) the width sizes of the plate surfaces of which are 1.1 mm and 0.8 mm have been described, the width size of the plate surface of the lead frame is not limited to the above-described size. Namely, the lead frame can produce the same effect as the above described lead frame (first lead frame and second lead frame) so long as the width size of the plate surface is set within the range from 0.5 mm to 2.0 mm.

Figure 8:
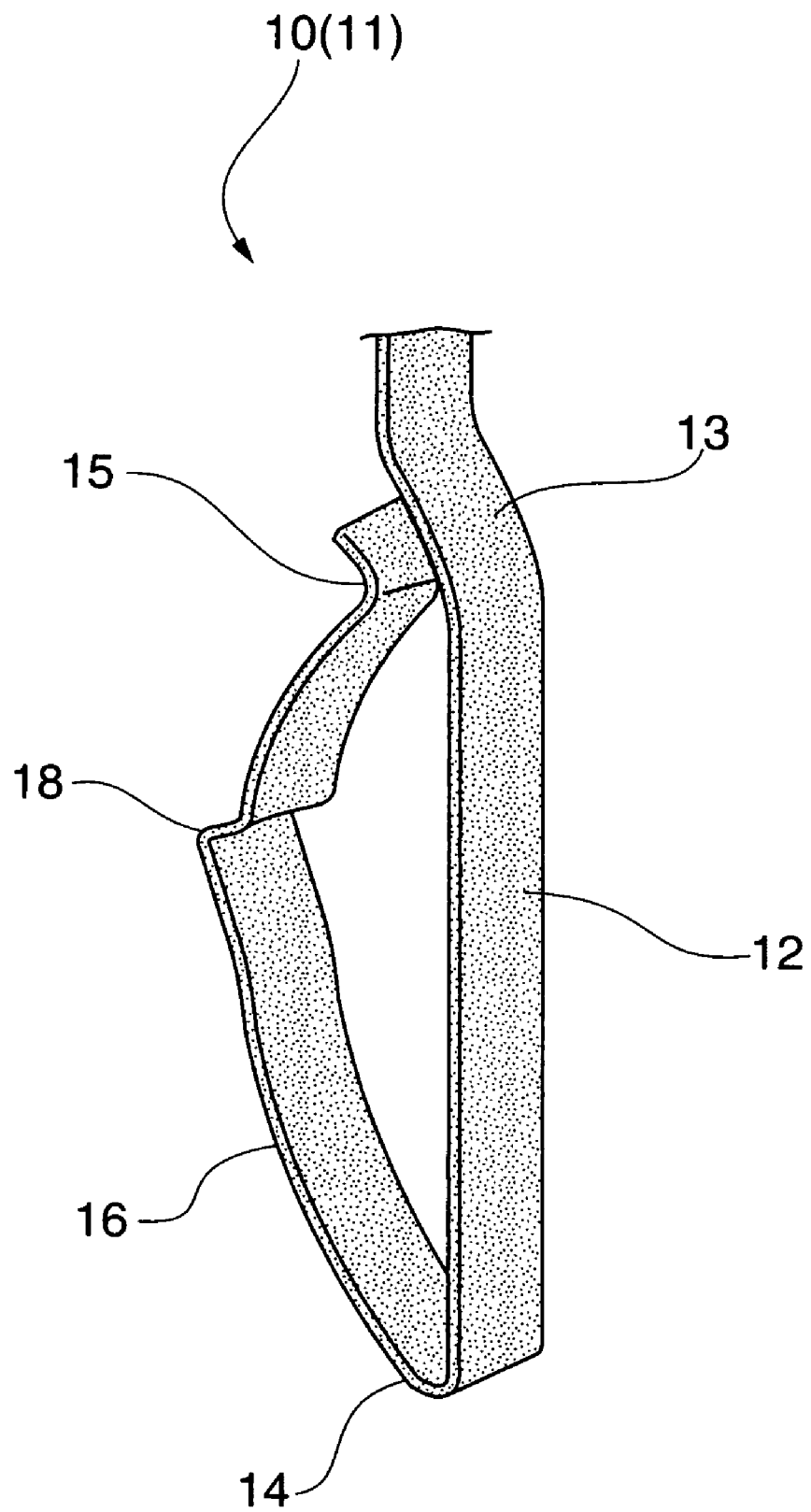
FIG. 8 is a perspective view showing an external appearance of a lead frame having a protrusion at a portion of an element abutment section, which is to be contact with an electrode terminal section of a detection element.
Figure 9:
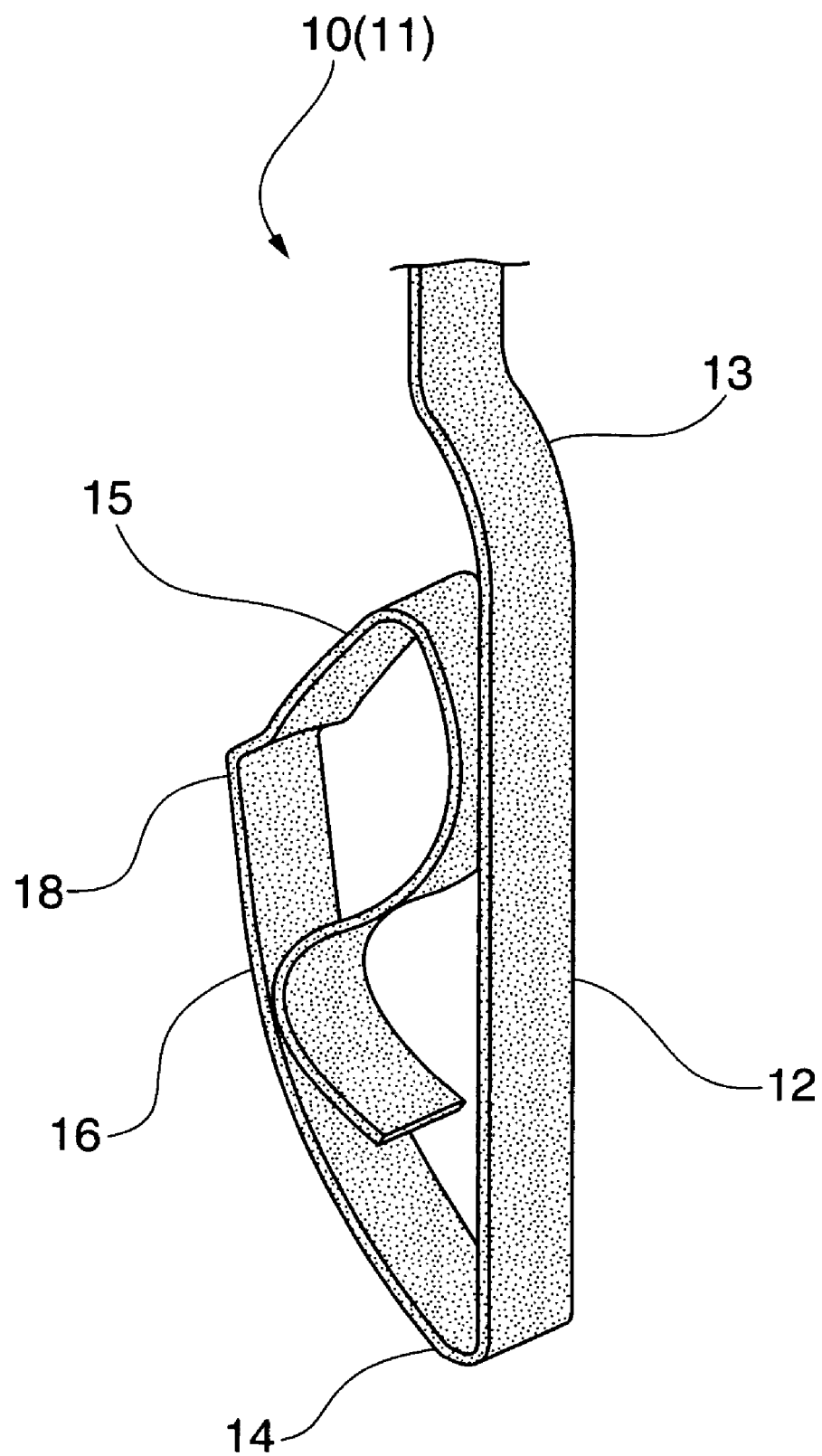
FIG. 9 is a perspective view showing an external appearance of a lead frame with a frame abutment portion of the element abutment section, which is formed into a curved shape.

Further, with a view to elevating the contact pressure between the lead frame 10 and the electrode terminal section of the detection element 4, the element abutment section 16 may be formed with, as shown in FIG. 8, a convex portion 18 that protrudes toward the electrode terminal section, at a part to be brought into contact with the electrode terminal section. A perspective view of the lead frame 10 with the element abutment section 16 including the convex portion 18 is shown in FIG. 8. In the meantime, in the lead frame 10 (first lead frame 11) shown in FIG. 8, illustration of the above-described first frame locking section 19 is omitted.

By providing the convex portion 18 to the part of the element abutment section 16, which is to be brought into contact with the electrode terminal section and bringing the apex of the convex portion 18 into contact with the electrode terminal section, in corporation with the above-described structure for two-point support of the element abutment section 16 relative to the frame main body section 12, the contact pressure of the element abutment section 16 for contact with the element abutment section 16 can be made further higher. In the meantime, while in FIG. 8 is shown an example of providing the convex portion 18 to the element abutment section 16 of the first lead frame 11, a similar convex portion may be provided to the second element abutment section 216 of the second lead frame 211.

Further, the frame abutment portion 15 of the element abutment section 16 of the lead frame 10 may be formed into a curved shape. Specifically, as shown in FIG. 8, the frame abutment portion 15 can be formed into a curved shape by curving the frame abutment portion 15 axially toward the rear end side and in a way as to go apart from the frame main body section 12 (in other words, by bending into a circular arc shape).

By forming the frame abutment section 15 into a curved shape in the above-described manner and abuttingly engaging the frame abutment section and the frame main body section with each other, it becomes possible to reduce the degree to which metallic powder is caused due to rubbing between the frame abutment section and the frame main body section 12 even in the case the sensor (wide-range air/fuel ratio sensor 2) is used under a condition of being attached to a vehicle or the like whose vibration is severe. By this, a bad influence on the electrically connected condition between the lead frame 10 and the electrode terminal section of the detection element can be effectively inhibited.

In the meantime, while in FIG. 8 is shown an example in which the frame abutment portion 15 of the element abutment section 16 of the first lead frame 11 is formed into a curved shape, the second frame abutment portion 215 of the second lead frame 211 may be formed into a similar curved shape. Further, the curved shape into which the frame abutment portion 15 is formed is not limited to the shape of curving axially toward the rear end side as shown in FIG. 8 but can be such a shape of curving axially toward the front end side and in a way as to go apart from the frame main body section 12.

Further, while in the above-described embodiment the folded-back section extending while being bent to change the direction of extension, from the front end of the frame main body section 12 (second frame main body section 212) of the lead frame 10 axially toward the rear end side has been shown as the element abutment section 16 (second element abutment section 216), the lead frame 10 may be disposed in the separator 82 in a way as to allow the frame main body section 12 (second frame main body section 212) to be disposed between the electrode terminal section of the detection element 4 and the folded-back section, and the frame main body section 12 may be formed into a curved shape to serve as an element abutment section for contact with the electrode terminal section of the detection element 4.

The invention claimed is:

1. A sensor comprising:
    a detection element in the form of an axially extending plate, having a front end side to face an object to be measured and formed with an electrode terminal section at a rear end side;
    a metallic terminal member formed from a metallic sheet material and contacting the electrode terminal section thereby being electrically connected thereto to form an electrical path; and
    a plurality of terminal members,
    characterized in that:
    the metallic terminal member includes an axially extending frame main body section, and a folded-back section extending while being bent to change the direction of extension, from a front end of the frame main body section axially toward a rear end side of the frame main body section; and
    the folded-back section includes a connection side end portion connected to a front end of the frame main body section and a frame abutment portion formed at a position closer to a rear end than the connection side end portion for abutting engagement with the frame main body section;
    the folded-back section constitutes an element abutment section that extends while being bent to change the direction of extension, from the front end of the frame main body section and is disposed between the electrode terminal section of the detection element and the frame main body section to contact the electrode terminal section; and
    the width size of the folded-back section is within the range from 0.5 mm to 2.0 mm;
    wherein the terminal members are different in the width size of the folded-back section.

2. A sensor according to claim 1, wherein the metallic terminal member is configured so that the frame abutment portion of the folded-back section is not abuttingly engaged with the frame main body section when the metallic terminal member is in a free condition before being electrically connected to the electrode terminal section of the detection element and the frame abutment portion is abuttingly engaged with the frame main body section when the metallic terminal member is electrically connected to the electrode terminal section to cause the folded-back section to be resiliently deformed toward the frame main body section.

3. A sensor according to claim 1, wherein the folded-back section includes a convex portion that protrudes toward the electrode terminal section of the detection element and contacts at an apex thereof the electrode terminal section.

4. A sensor according to claim 1, further comprising a separator that is disposed radially outside a rear end side of the detection element and made of an insulating material, wherein the metallic terminal member is held between the detection element and the separator while being put in a condition of the folded-back section being resiliently deformed toward the frame main body section.

5. A sensor according to claim 1, wherein the frame abutment portion of the folded-back section is formed into a curved shape.

6. A method of producing a sensor including a detection element in the form of an axially extending plate, having a front end side to face an object to be measured and formed with an electrode terminal section at a rear end side, a separator disposed radially outside of a rear end side of the detection element formed with an electrode terminal section and made of an insulating material, a metallic terminal member formed from a metallic sheet material and contacting the electrode terminal section thereby being electrically connected thereto to form an electrical path, and a plurality of terminal members, wherein the metallic terminal member includes an axially extending frame main body section and a folded-back section extending while being bent to change the direction of extension, from a front end of the frame main body section axially toward a rear end side of the frame main body section and disposed between the electrode terminal section of the detection element and the frame main body section, wherein the folded-back section includes a connection side end portion connected to a front end of the frame main body section and a frame abutment portion formed at a position closer to a rear end than the connection side end portion for abutting engagement with the frame main body section, wherein the folded-back section constitutes an element abutment section that extends while being bent to change the direction of extension, from the front end of the frame main body section and is disposed between the electrode terminal section of the detection element and the frame main body section to contact the electrode terminal section, wherein the width size of the folded-back section is within the range from 0.5 mm to 2.0 mm, wherein the metallic terminal member is configured so that the frame abutment portion of the folded-back section is not abuttingly engaged with the frame main body section when the metallic terminal member is in a condition before being electrically connected to the electrode terminal section of the detection element and the folded-back section is abuttingly engaged with the frame main body section when the metallic terminal member is electrically connected to the electrode terminal section to cause the folded-back section to be resiliently deformed toward the frame main body section, and wherein the terminal members are different in the width size of the folded-back section, the method comprising:
a first step of disposing the metallic terminal member in the separator;
a second step of pressing the detection element against the folded-back section thereby resiliently deforming the folded-back section toward the frame main body section and bringing the frame contact portion of the folded-back section into contact with the frame main body section; and
a third step of changing relative positions of the detection element and the separator in a way as to allow the separator to be disposed radially outside the detection element.

7. A sensor comprising:
a detection element in the form of an axially extending plate, having a front end side to face an object to be measured and formed with an electrode terminal section at a rear end side; and
a plurality of metallic terminal members, each of which is formed from a metallic sheet material and contacting the electrode terminal section thereby being electrically connected thereto to form an electrical path, characterized in that:
each of the metallic terminal members includes an axially extending frame main body section, and a folded-back section extending while being bent to change the direction of extension, from a front end of the frame main body section axially toward a rear end side of the frame main body section;
the folded-back section includes a connection side end portion connected to a front end of the frame main body section and a frame abutment portion formed at a position closer to a rear end than the connection side end portion for abutting engagement with the frame main body section; and
the metallic terminal members are different in the width size of the folded-back section.

8. A sensor according to claim 7, wherein each of the metallic terminal members is configured so that the frame abutment portion of the folded-back section is not abuttingly engaged with the frame main body section when the metallic terminal member is in a free condition before being electrically connected to the electrode terminal section of the detection element and the frame abutment portion is abuttingly engaged with the frame main body section when the metallic terminal member is electrically connected to the electrode terminal section to cause the folded-back section to be resiliently deformed toward the frame main body section.

9. A sensor according to claim 7, further comprising a separator that is disposed radially outside a rear end side of the detection element and made of an insulating material, wherein the metallic terminal member is held between the detection element and the separator while being put in a condition of the folded-back section being resiliently deformed toward the frame main body section.

10. A sensor according to claim 7, wherein the frame abutment portion of the folded-back section is formed into a curved shape.

11. A sensor according to claim 7, wherein the folded-back section constitutes an element abutment section that extends while being bent to change the direction of extension, from the front end of the frame main body section and is disposed between the electrode terminal section of the detection element and the frame main body section to contact the electrode terminal section.

12. A sensor according to claim 11, wherein the folded-back section includes a convex portion that protrudes toward the electrode terminal section of the detection element and contacts at an apex thereof the electrode terminal section.

13. A method of producing a sensor including a detection element in the form of an axially extending plate, having a front end side to face an object to be measured and formed with an electrode terminal section at a rear end side, a separator disposed radially outside of a rear end side of the detection element formed with an electrode terminal section and made of an insulating material, and a plurality of metallic terminal members, each of which is formed from a metallic sheet material and contacting the electrode terminal section thereby being electrically connected thereto to form an electrical path, wherein each of the metallic terminal members includes an axially extending frame main body section and a folded-back section extending while being bent to change the direction of extension, from a front end of the frame main body section axially toward a rear end side of the frame main body section and disposed between the electrode terminal section of the detection element and the frame main body section, wherein the folded-back section includes a connection side end portion connected to a front end of the frame main body section and a frame abutment portion formed at a position closer to a rear end than the connection side end portion for abutting engagement with the frame main body section, wherein the metallic terminal members are different in the width size of the folded-back section, and wherein each of the metallic terminal members is configured so that the frame abutment portion of the folded-back section is not abuttingly engaged with the frame main body section when the metallic terminal member is in a condition before being electrically connected to the electrode terminal section of the detection element and the folded-back section is abuttingly engaged with the frame main body section when the metallic terminal member is electrically connected to the electrode terminal section to cause the folded-back section to be resiliently deformed toward the frame main body section, the method comprising:
a first step of disposing the metallic terminal member in the separator;
a second step of pressing the detection element against the folded-back section thereby resiliently deforming the folded-back section toward the frame main body section and bringing the frame contact portion of the folded-back section into contact with the frame main body section; and
a third step of changing relative positions of the detection element and the separator in a way as to allow the separator to be disposed radially outside the detection element.

* * * * *